United States Patent [19]
Kashanchi

[11] Patent Number: 5,439,453
[45] Date of Patent: Aug. 8, 1995

[54] HYPODERMIC NEEDLE STORAGE APPARATUS

[76] Inventor: Behnam Kashanchi, 450 N. Bedford Dr., Beverly Hills, Calif. 90210

[21] Appl. No.: 217,691

[22] Filed: Mar. 25, 1994

[51] Int. Cl.$^6$ .................................................. A61M 5/32
[52] U.S. Cl. ................................. 604/263; 604/192; 24/557; 206/365
[58] Field of Search .............. 604/110, 192, 198, 199, 604/263; 206/364–367; 24/3 F, 487, 545, 557

[56] References Cited

U.S. PATENT DOCUMENTS

| | | | |
|---|---|---|---|
| 2,195,967 | 4/1940 | Liebmann | 24/557 X |
| 2,836,942 | 6/1958 | Miskel | 206/365 X |
| 4,471,512 | 9/1984 | Thalenfeld | 24/557 |
| 4,643,722 | 2/1987 | Smith, Jr. | 604/192 |
| 4,781,697 | 11/1988 | Slaughter | 604/192 |
| 4,872,552 | 10/1989 | Unger | 206/365 |
| 4,909,792 | 3/1990 | Norelli | 604/192 |
| 5,046,612 | 9/1991 | Mostarda et al. | 206/365 |
| 5,163,915 | 11/1992 | Holleron | 604/192 |
| 5,188,612 | 2/1993 | Herrington, Jr. et al. | 604/192 |

FOREIGN PATENT DOCUMENTS

| | | | |
|---|---|---|---|
| 9206724 | 4/1992 | WIPO | 604/192 |

Primary Examiner—John D. Yasko
Assistant Examiner—Adam J. Cermak
Attorney, Agent, or Firm—Michael A. Painter

[57] ABSTRACT

An apparatus for storing a hypodermic needle which is adapted to permit the hypodermic needle to be removed and later recapped by relative lateral movement between the apparatus and the needle. The storage apparatus comprises a cylindrical housing which is closed at one end into which the hypodermic needle may be mounted. The hypodermic needle includes an enlarged hub which engages the upper, open end of the housing. The cylindrical wall of the housing is longitudinally severed from the open upper end of the housing to the closed bottom end thereof and extending through the bottom end of the housing. Sheathing tabs are secured to the outer surface of the housing, the sheathing tabs being oriented on opposite sides of the severed slot in the housing. When suitable force is applied to the sheathing tabs, the longitudinal edges of the cylindrical wall of the housing which defines the severed slot are separated thereby permitting the hypodermic needle to be removed or resheathed through the lateral opening in the wall of the housing.

2 Claims, 1 Drawing Sheet

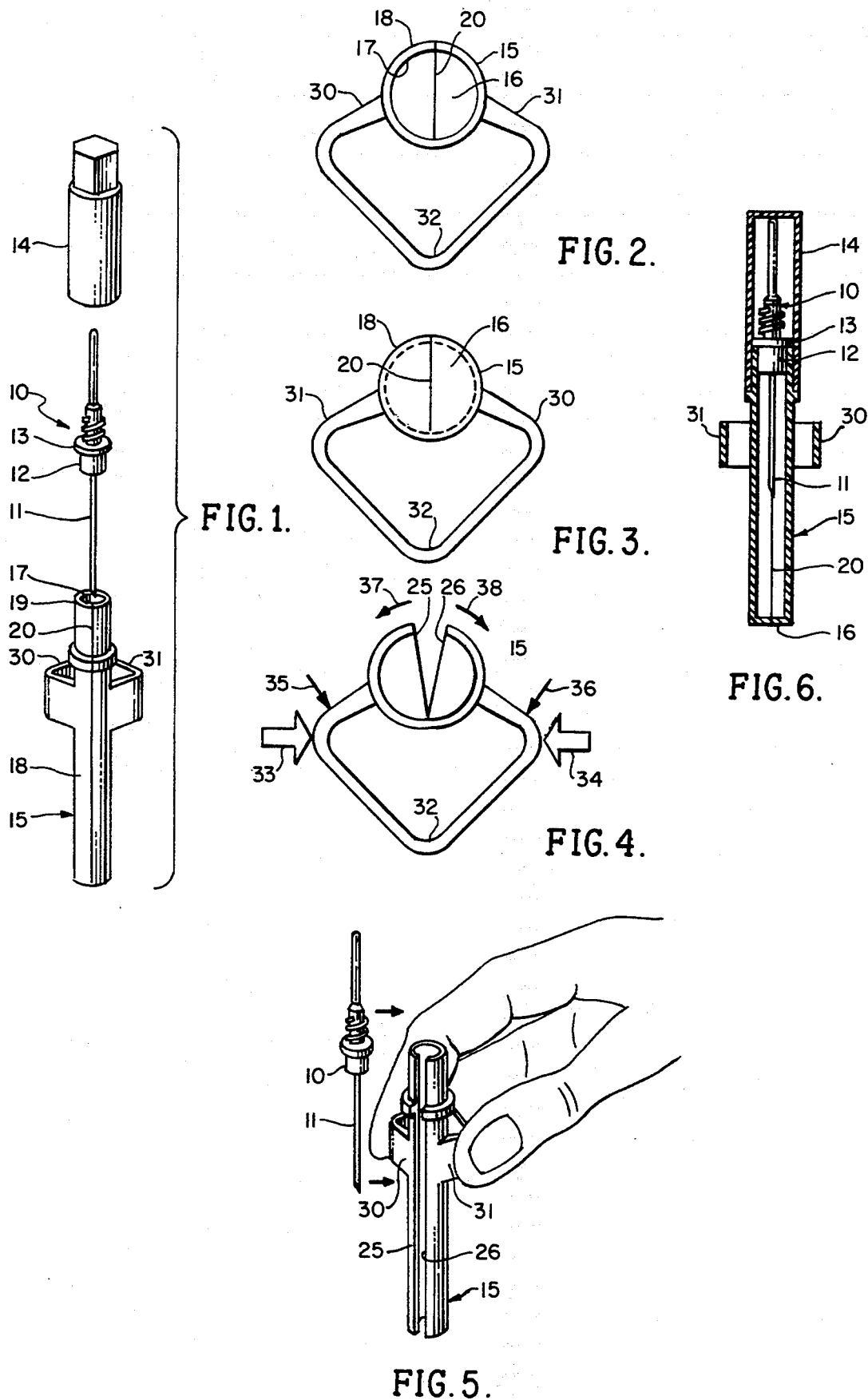

HYPODERMIC NEEDLE STORAGE APPARATUS

BACKGROUND OF THE INVENTION

1. Field of the Invention

The present invention generally relates to apparatus for storing and recapping hypodermic needles and, more particularly, those which will prevent inadvertent puncture wounds incurred when recapping the needle.

2. Prior Art

It is well recognized that modern medical procedures make extensive use of hypodermic needles for the purpose of giving injections, blood transfusions and for taking blood samples from a patient. One of the most frequent problems which occurs as a result of using hypodermic needles, catheters and the like is the occurrence of inadvertent puncture wounds which are suffered by the practitioner while attempting to recap the hypodermic needle after use. Such inadvertent punctures often require treatment of the injury and, most importantly, in many cases require the treatment of illnesses or diseases that may result from the puncture wounds. Where injuries or illnesses occur from inadvertent puncture wounds, the user may be faced with unacceptable financial expenditures and the loss of employee time.

The problems incident to inadvertent puncture wounds cannot be underestimated. As is now recognized, one of the most deadly diseases known to man, the HIV virus, can readily be transmitted through the use of contaminated needles. In addition, diseases such as herpes, syphilis, malaria and tuberculosis may be contracted by inadvertent puncture wounds by a hypodermic needle which has been used on a patient. To address this significant problem, the prior art discloses numerous devices which attempt to prevent the occurrence of inadvertent puncture wounds while recapping or resheathing a used hypodermic needle.

One of the devices disclosed by the prior art to reduce the problem of inadvertent puncture wounds utilizes a housing having a central hole in a finger-protecting shield that allows a hypodermic needle to be inserted therethrough while being grasped during the recapping procedure. The major problem associated with this type of design is that the point of the hypodermic needle must, by necessity, be moved longitudinally with respect to the axis of the shield. Therefore, opposed lateral movement of the hypodermic needle relative to the finger-protecting shields may still result in an inadvertent puncture wound.

Another device taught by the prior art provides for covering and uncovering the hypodermic needle by relative lateral movement between he needle housing and the hypodermic needle. An elongated housing is provided with an open, elongated slot which permits insertion of the hypodermic needle into the housing and removal of the needle therefrom by relative lateral movement between the housing and the needle. The elongated slot in the housing is covered by a removable cover which, after removal, results in the exposed opening defined by the slot. The problem inherent in this device results from the open, elongated slot. Once the covering member has been removed from the elongated slot, the hypodermic needle may be inadvertently dislodged from the housing thereby providing for a continued risk of inadvertent puncture wounds.

The present invention resolves those problems inherent in the devices taught by the prior art. The present invention provides an elongated housing which is adapted to hold a hypodermic needle along the axis of the housing. The cylindrical wall of the housing is sliced to create an opening along its longitudinal axis, the resilient forces of the cylindrical structure of the housing causing the boundaries of the severed wall to be maintained in contact thereby preventing inadvertent exposure of the hypodermic needle. Sheathing tabs are secured to the outer wall of the housing. The orientation of the sheathing tabs relative to the opening in the wall of the housing will permit separation of the housing walls along the severed interface when force is imposed upon the tabs. When force is imposed upon the tabs thereby separating the housing walls along the interface, the hypodermic needle may be removed from the housing or recapped within the housing by laterally moving the needle between the separated edges of the housing.

SUMMARY OF THE INVENTION

The present invention provides an apparatus for storing a hypodermic needle which substantially precludes the possibility of inadvertent puncture wounds. In the present invention, an elongated cylindrical housing is adapted to store a hypodermic needle before use and provides a safe enclosure for recapping and securing the needle after use. A cylindrical housing having an open upper end and closed bottom end is used to secure the hypodermic needle. The cylindrical wall is severed from the open upper end through and including the closed bottom end, the interface between the longitudinal surfaces of the severed cylindrical walls being aligned in parallel spaced relation to the longitudinal axis of the housing. In its quiescent form, the resiliency of the cylindrical housing will maintain the contact between the severed surfaces of the cylindrical walls. Sheathing tabs are affixed to the outer surface of the housing on opposite sides of the interface between the longitudinal wall edges. When appropriate forces are imposed upon the sheathing tabs, an elongated slot will be created at the interface exposing the interior of the housing. When the elongated slot is opened, the hypodermic needle may be removed or recapped by laterally moving the needle through the slot thereby avoiding any movement of the needle toward the hands of the user.

It is therefore an object of the present invention to provide an improved hypodermic needle storage apparatus.

It is another object of the present invention to provide a hypodermic needle storage apparatus which minimizes the hazards resulting from inadvertent needle punctures.

It is still another object of the present invention to provide a hypodermic needle storage apparatus which permits the hypodermic needle to be removed or recapped by relative lateral movement between a housing member and the needle.

It is still yet another object of the present invention to provide a hypodermic needle storage apparatus which is simple and inexpensive to fabricate.

The novel features which are believed to be characteristic of the invention, both as to its organization and method of operation, together with further objectives and advantages thereof, will be better understood from the following description considered in connection with the accompanying drawing in which a presently preferred embodiment of the invention is illustrated by way of example. It is to be expressly understood, however, that the drawing is for the purpose of illustration and description only, and is not intended as a definition of the limits of the invention.

BRIEF DESCRIPTION OF THE DRAWING

FIG. 1 is an assembly, perspective view of a hypodermic needle and the present invention storage apparatus.

FIG. 2 is a top, plan view of the present invention hypodermic needle storage apparatus.

FIG. 3 is a bottom plan view of the present invention storage apparatus.

FIG. 4 is a top, plan view of the storage apparatus in its open position.

FIG. 5 is a cross-sectional view of a hypodermic needle and the storage apparatus in assembled condition.

FIG. 6 is a schematic illustration showing the movement involved in recapping a hypodermic needle.

DESCRIPTION OF THE PRESENTLY PREFERRED EMBODIMENT

The present invention hypodermic needle storage apparatus can be best understood by reference to FIG. 1 wherein an assembly of a hypodermic needle within the storage apparatus can be best seen. In its general form, a hypodermic needle assembly 10 comprises the needle 11 and the collar 12. A seating hub 13 is typically used to align the hypodermic needle assembly 10 and is used to position the hypodermic needle assembly 10 within the present invention storage apparatus. A cylindrical housing 15 is open at the top end which is adapted to receive the hypodermic needle assembly 10 and has a closed member 16 at the bottom end thereof. A sealing cap 14 is a cylindrical member adapted to be slidingly fit over the top end 19 of housing 15 and secure needle assembly 10 within the storage apparatus.

The structure of housing 15 may be best seen in FIGS. 2, 3, 4 and 5. Housing 15 comprises a cylinder having annular inner and outer wall surfaces 17 and 18, respectively. Bottom closure member 16 is integral with the walls of housing 15. As stated hereinabove, it is an objective of the present invention to permit the removal and recapping of a hypodermic needle assembly 10 by laterally moving the needle 11 relative to housing 15. To accomplish this objective, the cylindrical wall of housing 15 is severed from the top end 19 through and including the bottom closure member 16 creating an interface 20 between longitudinal wall surfaces 25 and 26 defined by inner and outer walls 17 and 18, respectively. Interface 20 is in parallel spaced relation to the longitudinal axis of housing 15.

Housing 15 is constructed of a resilient, thermoplastic material which may be deformed when a force is applied thereto, but will return to its undeformed, quiescent condition when the force is removed. In order to allow hypodermic needle assembly 10 to be recapped in a manner contemplated by the present invention, a pair of sheathing tabs 30 and 31 are secured to outer surface 18 of housing 15 at an oblique angle relative to interface 20. Although the preferred embodiment of the present invention illustrates sheathing tabs 30 and 31 being coupled to one another by a bracing member 32, it is understood the scope of the present invention encompasses the use of uncoupled sheathing tabs 30 and 31.

The operation of the present invention may be best understood by reference to FIG. 5 and FIG. 6. When the user applies an inwardly directed force in the manner designated by reference numerals 33, 34, force components designated by reference numerals 35, 36 will cause housing 15 to be deformed with the resulting separation of longitudinal surfaces 25 and 26 in the directions designated by reference numerals 37 and 38, respectively. The deformation of housing 15 will be maintained so long as the inwardly directed forces 33, 34 are applied. As can be seen in FIG. 6, when longitudinal surfaces 25 and 26 are separated, hypodermic needle 10 may be recapped within housing 15 by moving the hypodermic needle assembly 10 laterally relative to housing 15 through the opening between longitudinal surfaces 25 and 26. Once needle 11 is properly disposed within the cavity of housing 15 and forces 33, 34 are removed (see FIG. 4), longitudinal surfaces 25 and 26 will be positioned adjacent one another and collar 12 and seating hub 13 positioned adjacent top end 19. Needle assembly 10 is fully recapped by slidably fitting cap 14 about outer wall 18 of housing 15.

It can therefore be seen the present invention provides an improved apparatus for storing and recapping hypodermic needles. When replacing a hypodermic needle after use, the needle 10 may be inserted within housing 15 by deforming the wall of housing 15 thereby separating longitudinal surfaces 25 and 26. When the longitudinal surfaces 25 and 26 are separated, needle 11 may be recapped by relative lateral movement between needle 11 and housing 15. The structure of the present invention and its manner of operation avoids the necessity of moving the point of needle 11 in the direction of the hand of a user thereby precluding inadvertent puncture wounds.

I claim:

1. A hypodermic needle assembly comprising:
   (a) a hypodermic needle having a tubular collar and a needle extending axially therethrough;
   (b) a needle housing for receiving and storing the hypodermic needle having a resilient, elongated cylindrical wall and an open end and a closed end, said cylindrical wall being severed from the top end to the closed bottom end defining adjacent elongated surfaces of said cylindrical wall being in parallel spaced relation to the axis of said housing;
   (c) first and second tabs, each having a top surface, said tabs being secured to said cylindrical wall and being equally spaced from the adjacent first and second elongated surfaces, the top surfaces of said tabs being obliquely oriented with respect to said adjacent elongated surfaces;
   (d) closure means for securing said hypodermic needle within said housing slidably coupled about the cylindrical wall of said housing adjacent the top end thereof; and
   (e) a bracing member coupled intermediate said first and second tabs.

2. A hypodermic needle storage apparatus comprising:
   (a) a resilient, elongated cylindrical housing having a wall defining an interior cavity for receiving and storing a hypodermic needle, said wall having an open first end and a closed second end, said wall having an elongated, longitudinally disposed slot disposed between the open first end to the closed second end and extending diametrically across said closed end, said slot being defined by adjacent longitudinal surfaces of said wall;

(b) first and second tabs, each having a top surface, said tabs being secured to said wall and being equally spaced from the adjacent longitudinal surfaces, the top surfaces of said tabs being obliquely oriented with respect to said adjacent longitudinal services; and (c) a bracing member coupled intermediate said first and second tabs.

* * * * *